(12) United States Patent
Ting (10) Patent No.: US 12,011,313 B2
(45) Date of Patent: Jun. 18, 2024

(54) STETHOSCOPE AND BINAURAL ASSEMBLY FOR A STETHOSCOPE INCLUDING A SOUND JUNCTION BLOCKAGE PREVENTION MEMBER

(71) Applicant: MDF Instruments USA LLC, Rincon, PR (US)

(72) Inventor: Darren Talun Chiao Ting, Rincon, PR (US)

(73) Assignee: MDF Instruments USA LLC, Rincon, PR (US)

( * ) Notice: Subject to any disclaimer, the term of this patent is extended or adjusted under 35 U.S.C. 154(b) by 0 days.

(21) Appl. No.: 17/966,248

(22) Filed: Oct. 14, 2022

(65) Prior Publication Data

US 2023/0120859 A1   Apr. 20, 2023

Related U.S. Application Data

(60) Provisional application No. 63/255,913, filed on Oct. 14, 2021.

(51) Int. Cl.
*A61B 7/02* (2006.01)
*G10K 13/00* (2006.01)

(52) U.S. Cl.
CPC ............... *A61B 7/02* (2013.01); *G10K 13/00* (2013.01)

(58) Field of Classification Search
CPC .......... A61B 7/02; G10K 13/00; G10K 11/08; G10K 11/22
USPC ........................................................ 181/131
See application file for complete search history.

(56) References Cited

U.S. PATENT DOCUMENTS

| 1,585,407 | A | * | 5/1926 | Morin | A61B 7/02 181/135 |
| 2,799,270 | A |   | 7/1957 | Simon | |
| 3,152,659 | A | * | 10/1964 | Littman | A61B 7/026 D24/134 |
| 3,168,160 | A | * | 2/1965 | Littman | A61B 7/02 181/135 |
| 4,569,413 | A | * | 2/1986 | Allen | A61B 7/026 181/131 |

(Continued)

FOREIGN PATENT DOCUMENTS

DE   2106249 A1   6/1977

*Primary Examiner* — Dedei K Hammond
*Assistant Examiner* — Jennifer B. Olson
(74) *Attorney, Agent, or Firm* — The Law Office of Patrick F. O'Reilly III, LLC (57) ABSTRACT

A stethoscope and binaural assembly are disclosed herein. The stethoscope includes a stethoscope chestpiece assembly and a binaural assembly including a first ear tube, a second ear tube, and an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube, the binaural assembly further including a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user.

20 Claims, 6 Drawing Sheets

(56) References Cited

U.S. PATENT DOCUMENTS

| | | | |
|---|---|---|---|
| 5,883,340 A * | 3/1999 | Shieh | A61B 7/02 |
| | | | 181/131 |
| 5,952,618 A | 9/1999 | DesLauriers | |
| 8,939,251 B2 | 1/2015 | Ting | |
| D724,206 S | 3/2015 | Ting | |
| D724,728 S | 3/2015 | Ting | |
| 9,486,180 B2 | 11/2016 | Ting | |
| D926,313 S | 7/2021 | Ting et al. | |
| 11,666,302 B2 | 6/2023 | Ting | |
| 2004/0226771 A1 | 11/2004 | Werblud | |
| 2014/0005574 A1 | 1/2014 | Ting | |
| 2015/0129350 A1 | 5/2015 | Ting | |
| 2021/0038183 A1 | 2/2021 | Ting | |

\* cited by examiner

STETHOSCOPE AND BINAURAL ASSEMBLY FOR A STETHOSCOPE INCLUDING A SOUND JUNCTION BLOCKAGE PREVENTION MEMBER

CROSS-REFERENCE TO RELATED APPLICATIONS

This patent application claims priority to, and incorporates by reference in its entirety, U.S. Provisional Patent Application No. 63/255,913, entitled "Stethoscope And Binaural Assembly For A Stethoscope Including A Sound Junction Blockage Prevention Member", filed on Oct. 14, 2021.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a stethoscope and a binaural assembly of a stethoscope. More particularly, the invention relates to a stethoscope and a stethoscope binaural assembly that include a sound junction blockage prevention member for preventing one or more internal sound passageways of a sound transmission junction of a stethoscope acoustic tube from becoming blocked.

2. Background

It is known in the art that a medical practitioner employs various devices during the course of examination of a patient. One such instrument is a stethoscope that is used by physicians, nurses, and paramedics in the early stage of any general examination and/or proper vital sign examination of a patient.

A stethoscope is an acoustic medical device for auscultation, or listening to the internal sounds of a body. It is often used to listen to heart sounds. It is also used to listen to intestines and blood flow in arteries and veins. Acoustic stethoscopes operate on the transmission of sounds from the chestpiece, via air-filled hollow tubes, to a binaural (headset) that a practitioner uses to listen to the acoustic sounds of a patient. The chestpiece usually consists of a diaphragm and a housing that supports the diaphragm within the chestpiece body. When the diaphragm is placed on the patient, body sounds vibrate the diaphragm, creating acoustic pressure waves which travel up the tubing to the binaural and the listener's ears.

The proper operation of a stethoscope is essential, since a practitioner, nurse or a doctor, uses a stethoscope to listen to the sounds of a patient's body to determine normal functioning and abnormalities.

The headsets of many conventional stethoscopes contain some type of spring in order to ensure that the ear tube members of the headset do not become inadvertently dislodged from the ears of a user (i.e., the spring essentially allows the stethoscope headset to gently clamp onto the user's head so that the ear tube members remain coupled to the user's ears). However, in these conventional headsets, when the ear tube members of the headset are flexed outwardly, the spring tends to deform in such a manner so as to obstruct a portion of the internal air passageway of the acoustic tube of the stethoscope. This obstruction of the internal air passageway of the acoustic tube of the stethoscope is highly undesirable because it makes it significantly more difficult for the user of the stethoscope to hear the internal sounds of a patient's body.

Therefore, what is needed is a stethoscope where a sound transmission junction of the stethoscope acoustic tube is not significantly blocked when the spring of the stethoscope headset is flexed outwardly by a user. In addition, a binaural assembly for a stethoscope is needed where a sound transmission junction of the acoustic tube is not significantly blocked when the spring of the headset is flexed outwardly by a user.

BRIEF SUMMARY OF EMBODIMENTS OF THE INVENTION

Accordingly, the present invention is directed to a stethoscope and binaural assembly for a stethoscope including a sound junction blockage prevention member that substantially obviates one or more problems resulting from the limitations and deficiencies of the related art.

In accordance with one or more embodiments of the present invention, there is provided a stethoscope that includes a stethoscope chestpiece assembly, the stethoscope chestpiece assembly including a chestpiece body and a diaphragm attached to the chestpiece body; and a binaural assembly, the binaural assembly including a first ear tube, a second ear tube, and an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube, the binaural assembly further including a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user.

In a further embodiment of the present invention, the sound transmission junction of the acoustic tube is in a form of a three-way sound transmission junction, and the one or more internal sound passageways of the sound transmission junction comprise a first internal sound passageway acoustically coupled to the stethoscope chestpiece, a second internal sound passageway acoustically coupled to the first ear tube, and a third internal sound passageway acoustically coupled to the second ear tube. In this further embodiment, sound waves emanating from the stethoscope chestpiece travel through the first internal sound passageway of the sound transmission junction, and then are conducted to the first ear tube by means of the second internal sound passageway of the sound transmission junction and to the second ear tube by means of the third internal sound passageway of the sound transmission junction.

In yet a further embodiment, the junction blockage prevention member comprises one or more tab members projecting outwardly from the at least one spring member at a location proximate to the sound transmission junction of the acoustic tube, the one or more tab members configured to prevent the at least one spring member from blocking the one or more internal sound passageways of the sound transmission junction by maintaining a predetermined gap between the at least one spring member and an internal wall of the acoustic tube.

In still a further embodiment, the one or more tab members of the junction blockage prevention member comprise a pair of spaced-apart tab members disposed on opposite sides of the at least one spring member.

In yet a further embodiment, the one or more tab members of the junction blockage prevention member are integrally formed with the at least one spring member.

In still a further embodiment, the junction blockage prevention member comprises a C-shaped spacer member attached to the at least one spring member at a location proximate to the sound transmission junction of the acoustic tube, the C-shaped spacer member configured to prevent the at least one spring member from blocking the one or more internal sound passageways of the sound transmission junction by maintaining a predetermined gap between the at least one spring member and an internal wall of the acoustic tube.

In yet a further embodiment, the C-shaped spacer member is attached to the at least one spring member by a fastener member.

In still a further embodiment, the junction blockage prevention member comprises a stent member disposed inside the sound transmission junction of the acoustic tube, the stent member including a stent body portion defining a plurality of stent sound passageways therein, the stent member configured to prevent the at least one spring member from blocking the one or more internal sound passageways of the sound transmission junction by maintaining unobstructed sound passageways through the stent body portion.

In yet a further embodiment, the plurality of stent sound passageways in the stent body portion are arranged in a T-shaped configuration.

In still a further embodiment, the stent member is affixedly attached to the at least one spring member.

In yet a further embodiment, the stethoscope further comprises a stent member disposed inside the sound transmission junction of the acoustic tube, the stent member including a stent body portion defining at least one stent sound passageway therein. In this further embodiment, the junction blockage prevention member comprises one or more tab members projecting outwardly from the at least one spring member at a location proximate to the sound transmission junction of the acoustic tube, the one or more tab members configured to prevent the at least one spring member from blocking the one or more internal sound passageways of the sound transmission junction by maintaining a predetermined gap between the at least one spring member and the stent.

In still a further embodiment, the one or more tab members of the junction blockage prevention member comprise a pair of spaced-apart tab members disposed on opposite sides of the at least one spring member.

In yet a further embodiment, the one or more tab members of the junction blockage prevention member are integrally formed with the at least one spring member.

In still a further embodiment, the first ear tube of the binaural assembly has a first earpiece disposed at a proximal end of the first ear tube, and the second ear tube of the binaural assembly has a second earpiece disposed at a proximal end of the second ear tube, the first earpiece configured to be inserted into a first ear of the user, and the second earpiece configured to be inserted into a second ear of the user.

In yet a further embodiment, the first earpiece is connected to the first ear tube by a first earpiece sleeve and the second earpiece is connected to the second ear tube by a second earpiece sleeve, the first and second earpiece sleeves configured to prevent damage to eardrums of the user resulting from one of the first and second earpieces becoming inadvertently detached from a respective one of the first and second ear tubes.

In accordance with one or more other embodiments of the present invention, there is provided a binaural assembly of a stethoscope that includes a first ear tube; a second ear tube; an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube; and a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user.

In a further embodiment of the present invention, the junction blockage prevention member comprises one or more tab members projecting outwardly from the at least one spring member at a location proximate to the sound transmission junction of the acoustic tube, the one or more tab members configured to prevent the at least one spring member from blocking the one or more internal sound passageways of the sound transmission junction by maintaining a predetermined gap between the at least one spring member and an internal wall of the acoustic tube.

In yet a further embodiment, the junction blockage prevention member comprises a C-shaped spacer member attached to the at least one spring member at a location proximate to the sound transmission junction of the acoustic tube, the C-shaped spacer member configured to prevent the at least one spring member from blocking the one or more internal sound passageways of the sound transmission junction by maintaining a predetermined gap between the at least one spring member and an internal wall of the acoustic tube.

In still a further embodiment, the junction blockage prevention member comprises a stent member disposed inside the sound transmission junction of the acoustic tube, the stent member including a stent body portion defining a plurality of stent sound passageways therein, the stent member configured to prevent the at least one spring member from blocking the one or more internal sound passageways of the sound transmission junction by maintaining unobstructed sound passageways through the stent body portion.

In yet a further embodiment, binaural assembly further comprises a stent member disposed inside the sound transmission junction of the acoustic tube, the stent member including a stent body portion defining at least one stent sound passageway therein. In this further embodiment, the junction blockage prevention member comprises one or more tab members projecting outwardly from the at least one spring member at a location proximate to the sound transmission junction of the acoustic tube, the one or more tab members configured to prevent the at least one spring member from blocking the one or more internal sound passageways of the sound transmission junction by maintaining a predetermined gap between the at least one spring member and the stent.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
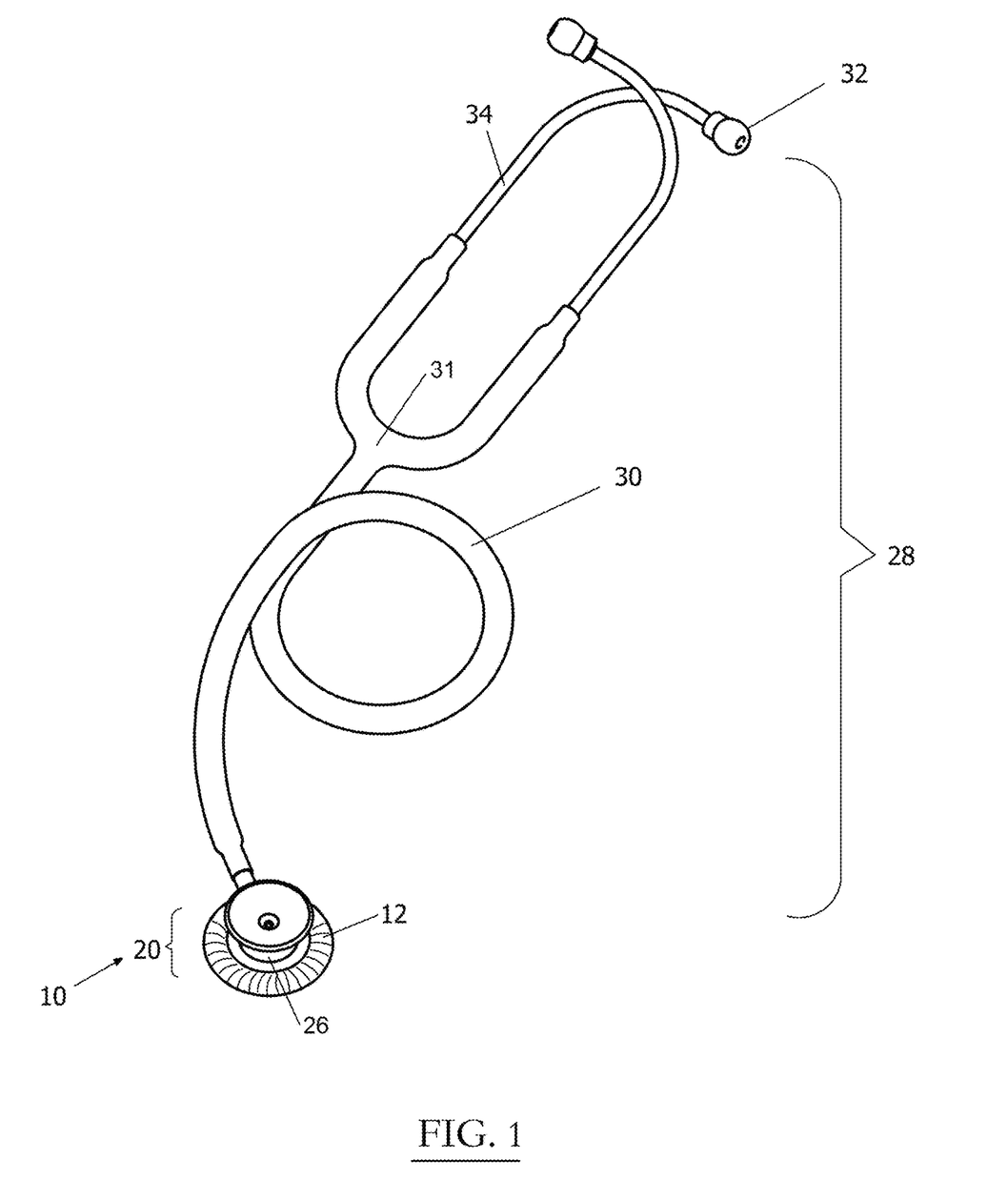
FIG. 1 is a perspective view of a stethoscope with a chestpiece having a sound junction blockage prevention member, according to an illustrative embodiment of the invention.

An illustrative embodiment of a stethoscope having a sound junction blockage prevention member is seen generally at 10 in FIG. 1. As shown in FIG. 1, the stethoscope 10 generally comprises a chestpiece assembly 20 and a binaural assembly 28 that includes two earpieces 32. Also, as illustrated in FIG. 1, the binaural assembly 28 of the stethoscope 10 includes an acoustic tube 30 that is acoustically coupled to a headset with two (2) ear tubes 34. Each of the ear tubes 34 is provided with a respective earpiece 32 disposed on a proximal end thereof. In addition, as shown in FIG. 1, the chestpiece 20 of the stethoscope 10 is provided with a diaphragm and ring 12 fitted thereon, which may comprise a one-piece diaphragm and ring.

Now, with reference again to FIG. 1, the illustrative embodiment of the chestpiece 20 of the stethoscope 10 will be described. As shown in this figure, it can be seen that the stethoscope chestpiece 20 generally includes a chestpiece body portion 26 having a first end and a second end, a frustoconical bell portion at the first end of the chestpiece body portion 26, and a diaphragm and ring 12 attached to the second end of the chestpiece body portion 26.

Turning again to FIG. 1, the illustrative embodiment of the binaural assembly 28 of the stethoscope 10 will be described. In the illustrative embodiment, the binaural assembly 28 generally includes first and second ear tubes 34, and an acoustic tube 30 connected to the first and second ear tubes 34. With combined reference to FIGS. 2, 5, and 6 it can be seen that the first ear tube 34 is flexibly connected to the second ear tube 34 by first and second spring members 14, 16 disposed inside the acoustic tube 30 (e.g., dual-leaf spring members 14, 16). In the illustrative embodiment, a portion of the lower spring member 16 is located proximate to a sound transmission junction 31 of the acoustic tube 30 (see FIG. 1). Also, as will be described in detail hereinafter with respect to FIGS. 3-6, the binaural assembly 28 further includes a particular type of junction blockage prevention member 24, 40, 44, 48. The junction blockage prevention member 24, 40, 44, 48 is configured to prevent the internal sound passageways of the sound transmission junction 31 of the acoustic tube 30 from becoming blocked or partially blocked by the spring members 14, 16 when the first and second ear tubes 34 are flexed outwardly away from one another by a user (i.e., the junction blockage prevention member 24, 40, 44, 48 is configured to prevent the spring members 14, 16 from diminishing the open space at the sound transmission junction 31).

Figure 2:
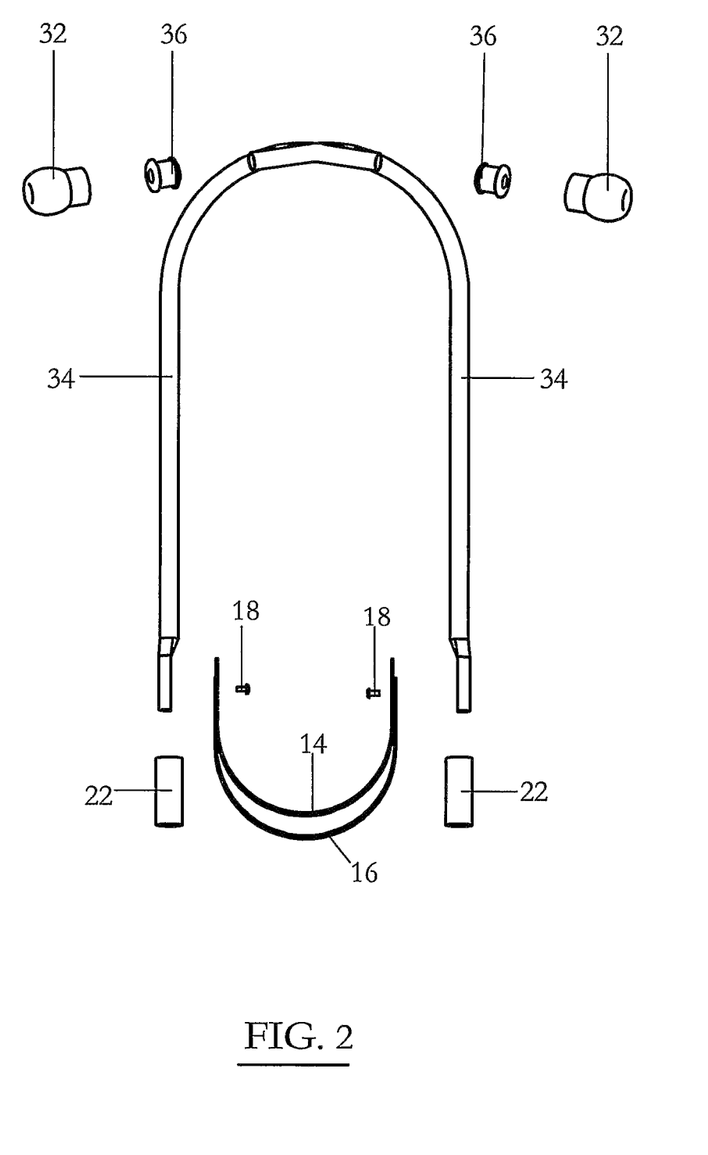
FIG. 2 is an exploded perspective view of a headset portion of a binaural assembly of a stethoscope, according to an illustrative embodiment of the invention.

In the illustrative embodiment, as shown in FIG. 2, the first and second spring members 14, 16 may be secured to one another and to distal ends of respective ear tubes 34 by respective rivets 18. In the illustrative embodiment, respective sleeves or fastener bushings 22 fit over the distal ends of the ear tubes 34 where the first and second spring members 14, 16 are attached to the ear tubes 34 by rivets 18. Also, in the illustrative embodiment, the first and second spring members 14, 16 may be made from a shape memory material that remembers a preferred spring force angle setting of the user for a better sealing in the ear canals of the user. In addition, in the illustrative embodiment, the second spring member 16 is slightly longer than the first spring member 14.

Figure 5:
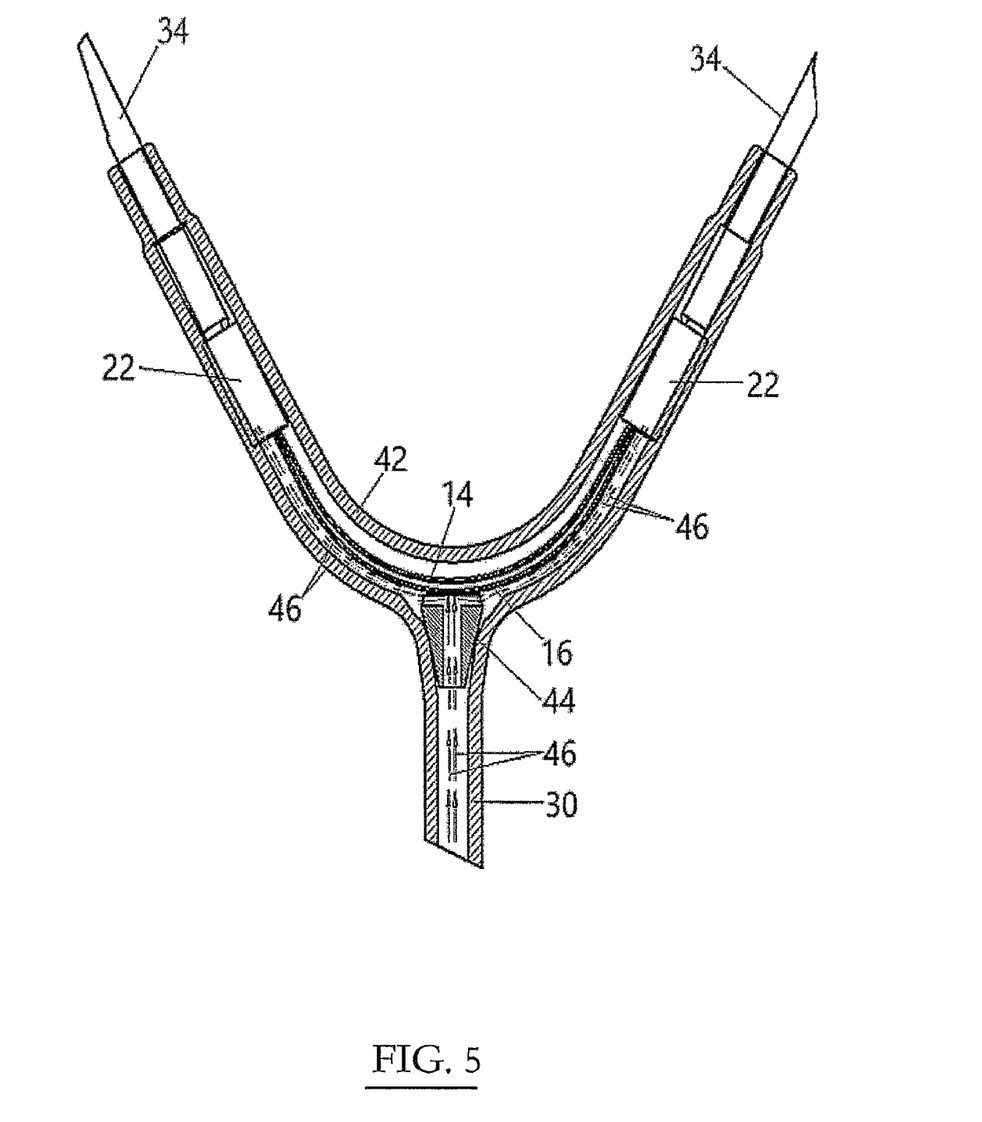
FIG. 5 is a sectional view of a portion of a stethoscope binaural assembly, according to still another illustrative embodiment of the invention, wherein a third type of junction blockage prevention member is provided at the sound transmission junction of the acoustic tube.
Figure 6:
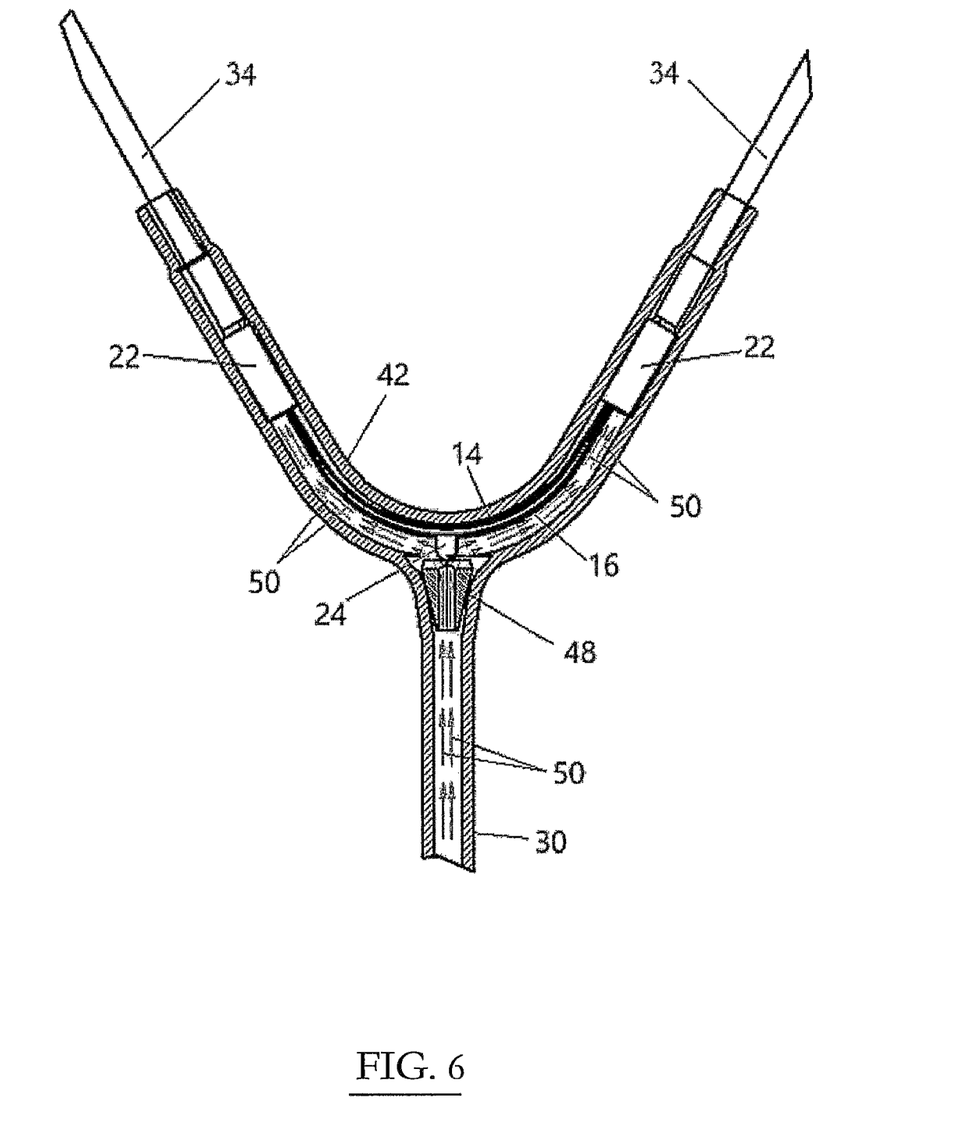
FIG. 6 is a sectional view of a portion of a stethoscope binaural assembly, according to yet another illustrative embodiment of the invention, wherein a fourth type of junction blockage prevention member is provided at the sound transmission junction of the acoustic tube.

With combined reference to FIGS. 1, 5, and 6, it can be that, in the illustrative embodiment, the sound transmission junction 31 of the acoustic tube 30 is in a form of a three-way sound transmission junction, and the internal sound passageways of the sound transmission junction 31 comprise a first internal sound passageway acoustically coupled to the stethoscope chestpiece 20, a second internal sound passageway acoustically coupled to the first ear tube 34, and a third internal sound passageway acoustically coupled to the second ear tube 34. In the illustrative embodiment, sound waves emanating from the stethoscope chestpiece 20 travel through the first internal sound passageway of the sound transmission junction 31, and then are conducted to the first ear tube 34 by means of the second internal sound passageway of the sound transmission junction and to the second ear tube 34 by means of the third internal sound passageway of the sound transmission junction.

Next, with combined reference to FIGS. 1 and 2, it can be seen that, in the illustrative embodiment, the first ear tube 34 of the binaural assembly 28 has a first earpiece 32 disposed at a proximal end of the first ear tube 34, and the second ear tube 34 of the binaural assembly 28 has a second earpiece 32 disposed at a proximal end of the second ear tube 34. The first earpiece 32 is configured to be inserted into a first ear of the user, and the second earpiece 32 is configured to be inserted into a second ear of the user. In the illustrative embodiment, referring to FIG. 2, the first earpiece 32 is connected to the first ear tube 34 by a first earpiece sleeve 36 and the second earpiece 32 is connected to the second ear tube 34 by a second earpiece sleeve 36. The first and second earpiece sleeves or bushings 36 are configured to prevent damage to eardrums of the user resulting from one of the first and second earpieces 32 becoming inadvertently detached from a respective one of the first and second ear tubes 34.

Figure 3:
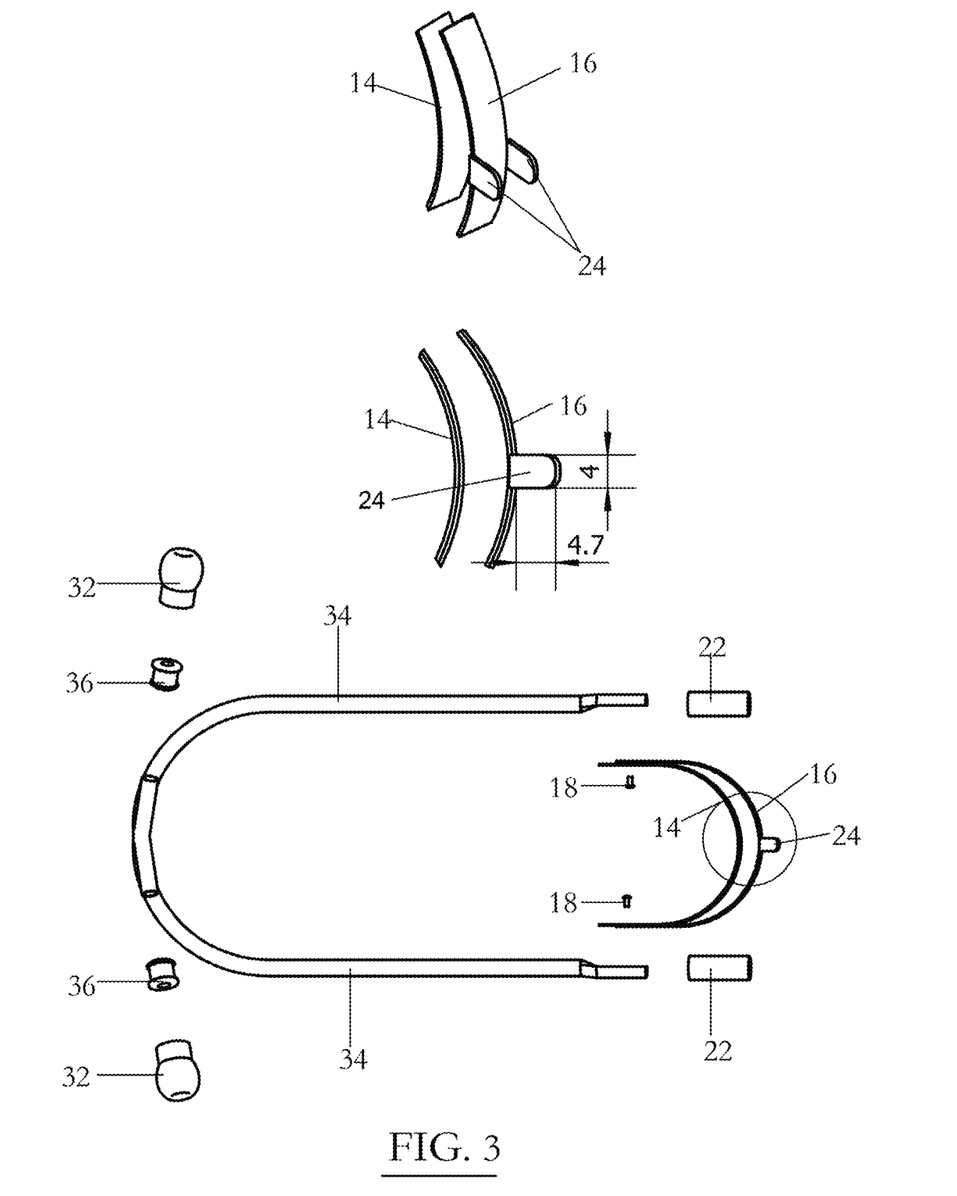
FIG. 3 is an exploded perspective view of a headset portion of a binaural assembly of a stethoscope, according to another illustrative embodiment of the invention, wherein the lower spring member of the headset is provided with a first type of junction blockage prevention member.

A first illustrative embodiment of the junction blockage prevention member 24 is shown in FIG. 3. Referring to this figure, it can be seen that the first type of junction blockage prevention member comprises a pair of spaced-apart tab members 24 disposed on opposite sides of the second spring member 16. In the first illustrative embodiment, the tab members 24 project outwardly from the second spring member 16 at a location proximate to the sound transmission junction 31 of the acoustic tube 30. The tab members 24 are configured to prevent the spring members 14, 16 from blocking the internal sound passageways of the sound transmission junction 31 by maintaining a predetermined gap between the spring member 16 and an internal wall of the acoustic tube 30.

In the illustrative embodiment, each of the spaced-apart tab members 24 are integrally formed with the second spring member 16 (e.g., formed from a single piece of metal). As shown in the detail view in the middle of FIG. 2, in the illustrative embodiment, each of spaced-apart tab members 24 may have a width of approximately 4.0 millimeters and a length of approximately 4.7 millimeters.

Figure 4:
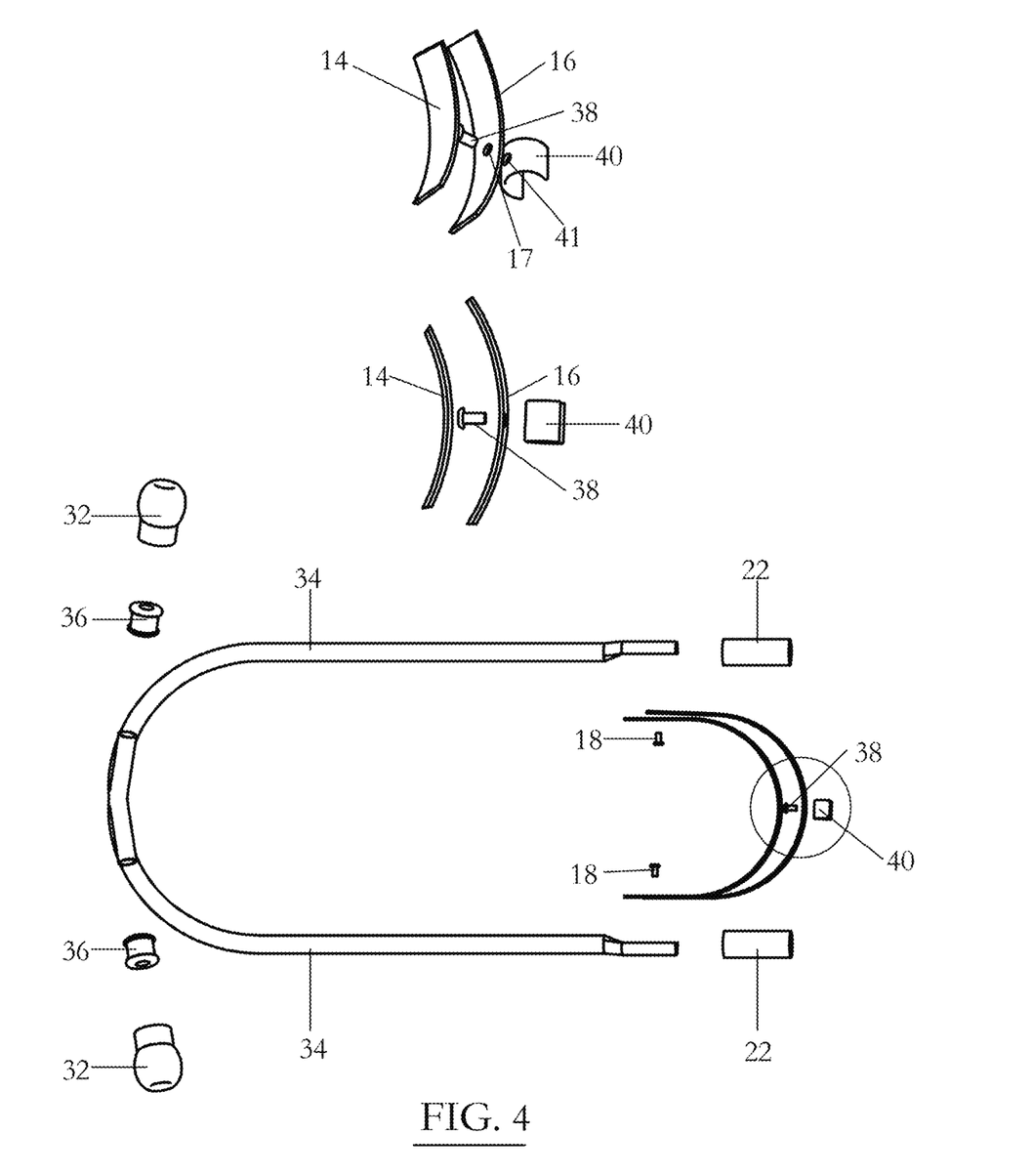
FIG. 4 is an exploded perspective view of a headset portion of a binaural assembly of a stethoscope, according to yet another illustrative embodiment of the invention, wherein a second type of junction blockage prevention member is attached to the lower spring member of the headset.

A second illustrative embodiment of the junction blockage prevention member 40 is shown in FIG. 4. Referring to this figure, it can be seen that the second type of junction blockage prevention member comprises C-shaped spacer member 40 attached to the second spring member 16 at a location proximate to the sound transmission junction of the acoustic tube 30. In the second illustrative embodiment, the C-shaped spacer member 40 is configured to prevent the second spring member 16 from blocking the internal sound passageways of the sound transmission junction 31 by maintaining a predetermined gap between the second spring member 16 and an internal wall of the acoustic tube 30.

As shown in the top detail view of FIG. 4, in the second illustrative embodiment, the C-shaped spacer member 40 is attached to the second spring member 16 by a fastener member (e.g., a rivet 38 that passes through a first aperture 17 in the second spring member 16 and a second aperture 41 in the C-shaped spacer member 40).

A third illustrative embodiment of the junction blockage prevention member 44 is shown in FIG. 5. Referring to this figure, it can be seen that the third type of junction blockage prevention member comprises a stent member 44 disposed inside the sound transmission junction 31 of the acoustic tube 30 with tube wall 42. In third illustrative embodiment of FIG. 5, it can be seen that the stent member 44 includes a stent body portion defining a plurality of stent sound passageways therein. The stent member 44 is configured to prevent the spring members 14, 16 from blocking the internal sound passageways of the sound transmission junction 31 by maintaining unobstructed sound passageways through the stent body portion.

In the third illustrative embodiment, the plurality of stent sound passageways in the stent body portion are arranged in a T-shaped configuration (refer to the stent 44 depicted in FIG. 5). In FIG. 5, the sound waves traveling upwardly through the acoustic tube 30 from the stethoscope chestpiece 20 are diagrammatically represented by the arrows 46. As shown in FIG. 5, the stent 44 prevents the sound waves traveling upwardly through the first internal sound passageway of the sound transmission junction 31 from being blocked by the spring members 14, 16 because the top of the stent 44 has branched passageways formed therein for maintaining a clear path for the sound waves that are traveling upwardly through the acoustic tube 30 from the stethoscope chestpiece 20.

In the third illustrative embodiment, the stent member is affixedly attached to the second spring member 16 (e.g., by welding or the like).

A fourth illustrative embodiment of the junction blockage prevention member 24, 48 is shown in FIG. 6. Referring to this figure, it can be seen that in the fourth illustrative embodiment, the binaural assembly 28 of the stethoscope 10 comprises a stent member 48 disposed inside the sound transmission junction 31 of the acoustic tube 30, the stent member 48 including a stent body portion defining a stent sound passageway therein. Also, in the fourth illustrative embodiment, the junction blockage prevention member comprises a pair of spaced-apart tab members 24 disposed on opposite sides of the second spring member 16, which are similar to the tab members 24 described above for the second illustrative embodiment. In the fourth illustrative embodiment, the spaced-apart tab members 24 project outwardly from the second spring member 16 at a location proximate to the sound transmission junction 31 of the acoustic tube 30. The spaced-apart tab members 24 are configured to prevent the spring members 14, 16 from blocking the internal sound passageways of the sound transmission junction 31 by maintaining a predetermined gap between the second spring member 16 and the stent 48 (i.e., the spaced-apart tab members 24 hold the internal passageway of the junction open).

In the fourth illustrative embodiment, similar to the second embodiment described above, each of the spaced-apart tab members 24 are integrally formed with the second spring member 16 (e.g., formed from a single piece of metal).

Referring again to FIG. 6, it can be seen that the sound waves traveling upwardly through the acoustic tube 30 from the stethoscope chestpiece 20 are diagrammatically represented by the arrows 50. As shown in FIG. 6, the stent 48 and the spaced-apart tab members 24 prevent the sound waves traveling upwardly through the first internal sound passageway of the sound transmission junction 31 from being blocked by the spring members 14, 16 because the bottom ends of the spaced-apart tab members 24 rest on the top of the stent 48 so as to maintain a clear path for the sound waves that are traveling upwardly through the acoustic tube 30 from the stethoscope chestpiece 20.

In the third and fourth illustrative embodiments, as shown in FIGS. 5 and 6, the stent members 44, 48 may have a pyramidal or frustoconical shape for being received in the first internal sound passageway of the sound transmission junction 31.

It is readily apparent that the aforedescribed stethoscope 10 and binaural assembly 28 offers numerous advantages. First of all, the sound transmission junction 31 of the stethoscope acoustic tube 30 of the stethoscope 10 described herein is not significantly blocked when the spring of the stethoscope headset is flexed outwardly by a user. Secondly, the sound transmission junction 31 of the acoustic tube 30 of the binaural assembly 28 is not significantly blocked when the spring of the headset is flexed outwardly by a user.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A stethoscope, comprising:
a stethoscope chestpiece assembly, the stethoscope chestpiece assembly including a chestpiece body and a diaphragm attached to the chestpiece body;
a binaural assembly, the binaural assembly including a first ear tube, a second ear tube, and an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube, the binaural assembly further including a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user; and
a stent member disposed inside the sound transmission junction of the acoustic tube, the stent member including a stent body portion defining at least one stent sound passageway therein; and
wherein the junction blockage prevention member comprises one or more tab members projecting outwardly from the at least one spring member at a location proximate to the sound transmission junction of the acoustic tube, the one or more tab members being configured to rest on a top of the stent body portion, and the one or more tab members configured to prevent the at least one spring member from blocking the one or more internal sound passageways of the sound transmission junction by maintaining a predetermined gap between the at least one spring member and the stent body portion.

2. The stethoscope according to claim 1, wherein the sound transmission junction of the acoustic tube is in a form of a three-way sound transmission junction, and the one or more internal sound passageways of the sound transmission junction comprise a first internal sound passageway acoustically coupled to the stethoscope chestpiece assembly, a second internal sound passageway acoustically coupled to the first ear tube, and a third internal sound passageway acoustically coupled to the second ear tube;
wherein sound waves emanating from the stethoscope chestpiece travel through the first internal sound passageway of the sound transmission junction, and then are conducted to the first ear tube by means of the second internal sound passageway of the sound transmission junction and to the second ear tube by means of the third internal sound passageway of the sound transmission junction.

3. The stethoscope according to claim 1, wherein the at least one stent sound passageway in the stent body portion comprises a plurality of stent sound passageways in the stent body portion.

4. The stethoscope according to claim 3, wherein the plurality of stent sound passageways in the stent body portion are arranged in a T-shaped configuration.

5. The stethoscope according to claim 1, wherein the one or more tab members of the junction blockage prevention member comprise a pair of spaced-apart tab members disposed on opposite sides of the at least one spring member.

6. The stethoscope according to claim 1, wherein the one or more tab members of the junction blockage prevention member are integrally formed with the at least one spring member.

7. The stethoscope according to claim 1, wherein the first ear tube of the binaural assembly has a first earpiece disposed at a proximal end of the first ear tube, and the second ear tube of the binaural assembly has a second earpiece disposed at a proximal end of the second ear tube, the first earpiece configured to be inserted into a first ear of the user, and the second earpiece configured to be inserted into a second ear of the user.

8. The stethoscope according to claim 7, wherein the first earpiece is connected to the first ear tube by a first earpiece sleeve and the second earpiece is connected to the second ear tube by a second earpiece sleeve, the first and second earpiece sleeves configured to prevent damage to eardrums of the user resulting from one of the first and second earpieces becoming inadvertently detached from a respective one of the first and second ear tubes.

9. The stethoscope according to claim 1, wherein the at least one spring member disposed inside the acoustic tube comprises a dual leaf spring with an upper spring member and a lower spring member, and the one or more tab members project outwardly from the lower spring member at the location proximate to the sound transmission junction of the acoustic tube.

10. A binaural assembly of a stethoscope, comprising:
a first ear tube;
a second ear tube;
an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube;
a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user; and
a stent member disposed inside the sound transmission junction of the acoustic tube, the stent member including a stent body portion defining at least one stent sound passageway therein; and
wherein the junction blockage prevention member comprises one or more tab members projecting outwardly from the at least one spring member at a location proximate to the sound transmission junction of the acoustic tube, the one or more tab members being configured to rest on a top of the stent body portion, and the one or more tab members configured to prevent the at least one spring member from blocking the one or more internal sound passageways of the sound transmission junction by maintaining a predetermined gap between the at least one spring member and the stent body portion.

11. The binaural assembly according to claim 10, wherein the one or more tab members of the junction blockage prevention member comprise a pair of spaced-apart tab members disposed on opposite sides of the at least one spring member.

12. The binaural assembly according to claim 10, wherein the one or more tab members of the junction blockage prevention member are integrally formed with the at least one spring member.

13. The binaural assembly according to claim 10, wherein the first ear tube of the binaural assembly has a first earpiece disposed at a proximal end of the first ear tube, and the second ear tube of the binaural assembly has a second earpiece disposed at a proximal end of the second ear tube, the first earpiece configured to be inserted into a first ear of the user, and the second earpiece configured to be inserted into a second ear of the user.

14. The binaural assembly according to claim 13, wherein the first earpiece is connected to the first ear tube by a first earpiece sleeve and the second earpiece is connected to the second ear tube by a second earpiece sleeve, the first and second earpiece sleeves configured to prevent damage to eardrums of the user resulting from one of the first and second earpieces becoming inadvertently detached from a respective one of the first and second ear tubes.

15. The binaural assembly according to claim 10, wherein the at least one spring member disposed inside the acoustic tube comprises a dual leaf spring with an upper spring member and a lower spring member, and the one or more tab members project outwardly from the lower spring member at the location proximate to the sound transmission junction of the acoustic tube.

16. A stethoscope, comprising:
a stethoscope chestpiece assembly, the stethoscope chestpiece assembly including a chestpiece body and a diaphragm attached to the chestpiece body; and
a binaural assembly, the binaural assembly including a first ear tube, a second ear tube, and an acoustic tube connected to the first and second ear tubes, the first ear tube being flexibly connected to the second ear tube by at least one spring member disposed inside the acoustic tube, a portion of the at least one spring member being located proximate to a sound transmission junction of the acoustic tube, the binaural assembly further including a junction blockage prevention member, the junction blockage prevention member configured to prevent one or more internal sound passageways of the sound transmission junction of the acoustic tube from becoming blocked or partially blocked by the at least one spring member when the first and second ear tubes are flexed outwardly away from one another by a user;
wherein the junction blockage prevention member comprises a pair of spaced-apart tab members or a C-shaped spacer member attached to the at least one spring member at a location proximate to the sound transmission junction of the acoustic tube, the pair of spaced-apart tab members or the C-shaped spacer member defining a downwardly facing channel, and the pair of spaced-apart tab members or the C-shaped spacer member configured to prevent the at least one spring member from blocking the one or more internal sound passageways of the sound transmission junction by maintaining a predetermined gap between the at least one spring member and an internal wall of the acoustic tube.

17. The stethoscope according to claim 16, wherein the junction blockage prevention member comprises the pair of spaced-apart tab members attached to the at least one spring member, and the pair of spaced-apart tab members defines the downwardly facing channel.

18. The stethoscope according to claim 17, wherein the pair of spaced-apart tab members are integrally formed with the at least one spring member.

19. The stethoscope according to claim 16, wherein the junction blockage prevention member comprises the C-shaped spacer member attached to the at least one spring member at the location proximate to the sound transmission junction of the acoustic tube, the C-shaped spacer member including a first prong member and a second prong member, and the first prong member being spaced apart from the second prong member by the downwardly facing channel.

20. The stethoscope according to claim 19, wherein the C-shaped spacer member is attached to the at least one spring member by a fastener member.

* * * * *